(12) United States Patent
Kapa et al.

(10) Patent No.: US 7,589,216 B2
(45) Date of Patent: Sep. 15, 2009

(54) PROCESS FOR PREPARING N-HYDROXYFORMAMIDO-PROPYL PYRROLIDIN COMPOUNDS AND INTERMEDIATES

(75) Inventors: Prasad Koteswara Kapa, Parsippany, NJ (US); Xinglong Jiang, Hillsborough, NJ (US); Eric M. Loeser, Scotch Plains, NJ (US); Joel Slade, Flanders, NJ (US); Mahavir Prashad, Montville, NJ (US); George Tien-San Lee, Towaco, NJ (US)

(73) Assignee: Novartis AG, Basel (CH)

( * ) Notice: Subject to any disclaimer, the term of this patent is extended or adjusted under 35 U.S.C. 154(b) by 787 days.

(21) Appl. No.: 10/527,628

(22) PCT Filed: Sep. 18, 2003

(86) PCT No.: PCT/EP03/10416

§ 371 (c)(1),
(2), (4) Date: May 25, 2005

(87) PCT Pub. No.: WO2004/026824

PCT Pub. Date: Apr. 1, 2004

(65) Prior Publication Data

US 2005/0261504 A1 Nov. 24, 2005

Related U.S. Application Data

(60) Provisional application No. 60/411,920, filed on Sep. 19, 2002, provisional application No. 60/480,242, filed on Jun. 20, 2003.

(51) Int. Cl.
C07D 277/04 (2006.01)
C07D 207/16 (2006.01)

(52) U.S. Cl. .................. 548/537; 548/540; 548/200; 537/533; 546/279.1; 514/340

(58) Field of Classification Search ............... 548/537, 548/200; 546/279.1; 514/340
See application file for complete search history.

(56) References Cited

U.S. PATENT DOCUMENTS

| 4,115,417 | A | 9/1978 | Valentine |
| 4,384,139 | A | 5/1983 | Takehisa et al. |
| 6,423,690 | B1 | 7/2002 | Hunter et al. |
| 2002/0015678 | A1 | 2/2002 | Yuan et al. |
| 2003/0045479 | A1 | 3/2003 | Alvarez et al. |
| 2003/0069223 | A1 | 4/2003 | Jacobs et al. |

FOREIGN PATENT DOCUMENTS

| EP | 0 354 529 | 2/1990 |
| WO | 99/39704 | 8/1999 |
| WO | 02/070541 | 9/2002 |
| WO | 02/102790 | 12/2002 |
| WO | 2004/026824 | 4/2004 |
| WO | 2004/076053 | 9/2004 |
| WO | 2004/087133 | 10/2004 |
| WO | 2005/000835 | 1/2005 |

OTHER PUBLICATIONS

Geffken et al., "Darstellung von Derivaten der 3-Hydroxypropiohydroxamsäure unter Anwendung der Carbodiimid-Methode", Chemische Berichte, vol. 106, pp. 2246-2254 (1973).
Jin et al., "A Practical Method for the Conversion of Beta-Hydroxy Carboxylic Acids into the Corresponding Beta-Amino Acids", vol. 11, pp. 1189-1190 (1998).
Jin et al., "Inhibition Stereochemistry of Hydroxamate Inhibitors for Thermolysin", Bioorganic & Medicinal Chemistry Letters, vol. 8, No. 24, pp. 3515-3518 (1998).
Miller et al., "Synthesis of Beta-Lactams from Substituted Hydroxamic Acids", Journal of the Americal Chemical Society, vol. 102, No. 23, pp. 7026-7032 (1980).
Pfeffer et al., ".Alpha. Anions of Carboxylic Acids. V. Simple High Yield Preparation of .Alpha.-Alkylhydracrylic Acids and .Alpha.-Alkylacrylic Acids", Journal of Organic Chemistry, vol. 37, No. 8, pp. 1256-1258 (1972).
Rabinowitz et al., "Design of Selective and Soluble Inhibitors of Tumor Necrosis Factor-Alpha Converting Enzyme (TACE)", Journal of Medicinal Chemistry, vol. 44, pp. 4252-4267 (2001).
Ramaswami et al., "Terpenoids. IL. The Prins Reaction on the Isopropylidene-Type Double Bonds", Journal of Organic Chemistry, vol. 29, vol. 8, pp. 2245-2248 (1964).
Sakaki et al., "Synthesis of 1,3-Dioxin-4-Ones and Their use in Synthesis. XVIII. Synthesis of Azetidin-2-Ones from 1,3-Dioxin-4-Ones via 3-Hydroxycarboxamides", Chemical & Pharmaceutical Bulletin, vol. 37, No. 11, pp. 2952-2960 (1989).
Von Roedern et al., "Design and Synthesis of Malonic Acid-Based Inhibitors of Human Neutrophil Collagenase (MMP8)", Journal of Medicinal Chemistry, vol. 41, No. 3, pp. 339-345 (1998).
Chang et al., "Methionine Aminopeptidase Gene of *Escherichia coli* is Essential for Cell Growth", J. Bacteriol., vol. 171, No. 7, pp. 4071-4072 (1989).
Meinnel et al., Characterization of the Thermus thermophilus Locus Encoding Peptide Deformylase and Methionyl-tRNA$_f^{Met}$ Formyltransferase, J. Bacteriol., vol. 176, No. 23, pp. 7387-7390 (1994).
Mazel et al., "Genetic Characterization of Polypeptide Deformylase, a Distinctive Enzyme of Eubacterial Translation", EMBO J., vol. 13, pp. 914-923 (1994).

*Primary Examiner*—Kamal A Saeed
*Assistant Examiner*—Valerie Rodriguez-Garcia
(74) *Attorney, Agent, or Firm*—McCarter & English, LLP; Elizabeth A. Hanley; Joshua K. Roth

(57) ABSTRACT

The present invention is directed to a process for preparing intermediates that are useful to prepare certain antibacterial N-formyl hydroxylamine compounds which are peptide deformylase inhibitors. The process makes use α β-lactam intermediate. Certain optically pure intermediates are also claimed.

9 Claims, No Drawings

PROCESS FOR PREPARING N-HYDROXYFORMAMIDO-PROPYL PYRROLIDIN COMPOUNDS AND INTERMEDIATES

This application claims benefit of U.S. Provisional Application No. 60/411,920, filed Sep. 19, 2002, and U.S. Provisional Application No. 60/480,242, filed Jun. 20, 2003 which in their entirety are herein incorporated by reference.

This invention is directed to a process for preparing intermediates that are useful to prepare certain antibacterial N-formyl hydroxylamine compounds.

Peptide deformylase is a metallopeptidase found in prokaryotic organisms such as bacteria. Protein synthesis in prokaryotic organisms begins with N-formyl methionine (fMet). After initiation of protein synthesis, the formyl group is removed by the enzyme peptide deformylase (PDF); this activity is essential for maturation of proteins. It has been shown that PDF is required for bacterial growth (see Chang et al., J. Bacteriol., Vol. 171, pp. 4071-4072 (1989); Meinnel et al., J. Bacteriol, Vol. 176, No. 23, pp. 7387-7390 (1994); Mazel et al., EMBO J., Vol. 13, No. 4, pp. 914-923 (1994)). Since protein synthesis in eukaryotic organisms does not depend on fMet for initiation, agents that will inhibit PDF are attractive candidates for development of new anti-microbial and anti-bacterial drugs.

Co-pending application Ser. No. 10/171,706, filed Jun. 14, 2002 (incorporated herein by reference in its entirety) and WO02/102790, disclose novel N-formyl hydroxylamine compounds that inhibit PDF and are therefore useful as antibacterial agents. The compounds disclosed therein are certain N-[1-oxo-2-alkyl-3-(N-hydroxyformamido)-propyl]-(carbonylamino-aryl or -heteroaryl)-azacyclo$_{4-7}$alkanes or thiazacyclo$_{4-7}$alkanes which are described in more detail hereinafter. An improved process has been discovered for preparing intermediates useful for preparing these N-[1-oxo-2-alkyl-3-(N-hydroxyformamido)-propyl]-(carbonylamino-aryl or -heteroaryl)-azacyclo$_{4-7}$alkanes or thiazacyclo$_{4-7}$alkanes which makes use of a particular β-lactam intermediate.

The present invention is directed to a novel process for preparing certain intermediates which are useful to prepare certain N-formyl hydroxylamine compounds which are useful for inhibiting bacteria.

More specifically, the present invention is directed to a process for preparing a compound of the formula (VIII)

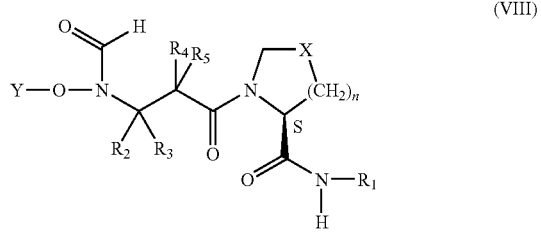

comprising Step A:

contacting a compound of the formula (I)

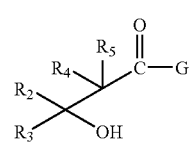

with a compound of the formula (II)

$$Y-O-NH_2 \qquad (II)$$

in the presence of a carboxy-activating agent, in a suitable solvent under conditions suitable to form a compound of the formula (III)

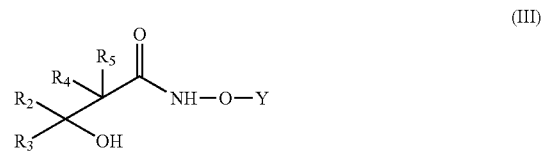

followed by Step B:

contacting compound (III) with a compound of the formula (XIII)

$$R'-SO_2-X' \qquad (XIII)$$

in the presence of a base in a suitable solvent, under conditions suitable to form a compound of the formula (IV)

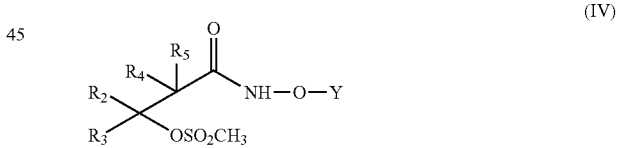

followed by Step C:

contacting compound (IV) with a base in a suitable solvent under conditions suitable to form a compound of the formula (V)

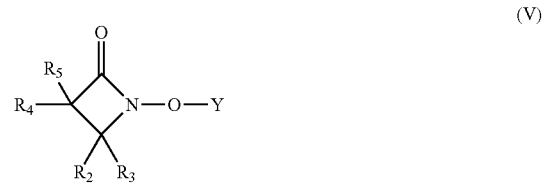

followed by Step D:

contacting compound (V) with a compound of the formula (VI)

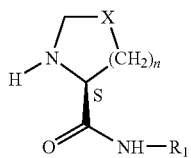
(VI)

in a suitable solvent optionally in the presence of an activator under conditions suitable to form a compound of the formula (VII)

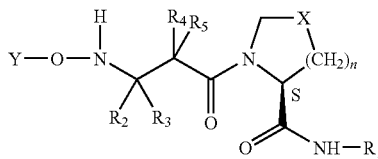
(VII)

followed by Step E:

contacting compound (VII) with a formylating agent in a suitable solvent under conditions suitable to form compound (VIII);

wherein
Y is a hydroxy protecting group;
each of $R_2$, $R_3$, $R_4$ and $R_5$ is independently hydrogen or an aliphatic group, or ($R_2$ and $R_3$) and/or ($R_4$ and $R_5$) collectively form a $C_{4-7}$cycloalkyl;
X is —$CH_2$—, —S—, —CH(OH)—, —CH(OR)—, —CH(SH)—, —CH(SR)—, —$CF_2$—, —C=N(OR)— or —CH(F)—;
wherein
R is alkyl;
G is —OH or —O$^\ominus$M$^\oplus$, wherein M is a metal or an ammonium moiety;
$R_1$ is aryl or heteroaryl;
X' is halo;
R' is alkyl or aryl; and
n is 0 to 3, provided that when n is 0, X is —$CH_2$—.

When the desired product is an N-oxide of an aromatic moiety having a nitrogen heteroatom, e.g., when $R_1$ is formula (X), (XIa) or (Xb), typically a pyridine derivative, it is necessary to perform an additional step after Step E, i.e., to oxidize the N of the aromatic ring (Step F). Therefore, the present invention includes Step F which comprises contacting the compound of formula (VIII), wherein $R_1$ is heteroaryl having an N heteroatom, with an oxidizing agent to form the corresponding N-oxide derivative.

In addition to the above process comprising Steps A through E or F, the present invention is directed to each of the steps individually, and to any two or more sequential steps.

DETAILED DESCRIPTION OF THE INVENTION

In particular, the present invention provides a process for preparing intermediates useful in the preparation of a N-[1-oxo-2-alkyl-3-(N-hydroxyformamido)-propyl]-(carbonylamino-aryl or -heteroaryl)-azacyclo$_{4-7}$alkane or thiazacyclo$_{4-7}$alkane, e.g., a compound of formula (IX)

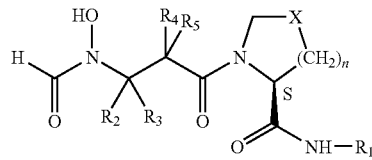
(IX)

wherein $R_1$, $R_2$, $R_3$, $R_4$, $R_5$, X and n are as defined above.

To convert the compound of formula (VIII) to the compound of formula (IX), the hydroxy protecting group is removed using conventional hydrogenolysis techniques known in the art, e.g., by contacting the compound of formula (VIII) with a palladium catalyst, such as Pd/BaSO$_4$.

The $R_1$ moiety can be a heteroaryl, e.g., an azacyclo$_{4-7}$ alkane, a thiazacyclo$_{4-7}$alkane or an imidazacyclo$_{4-7}$alkane. Specific examples of $R_1$ moieties in the compounds disclosed herein are heteroaryls of formula (X)

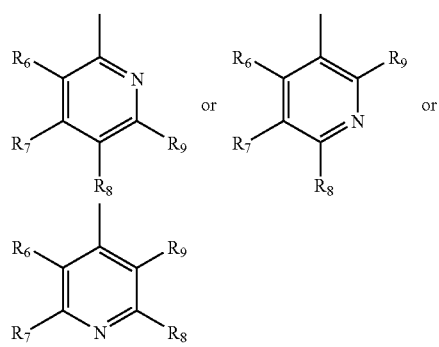
(X)

wherein each of $R_6$, $R_7$, $R_8$ and $R_9$, independently, is hydrogen, alkyl, substituted alkyl, hydroxy, alkoxy, acyl, acyloxy, SCN, halogen, cyano, nitro, thioalkoxy, phenyl, heteroalkylaryl, alkylsulfonyl or formyl.

A more specific $R_1$ moiety is a heteroaryl of formula (XIa)

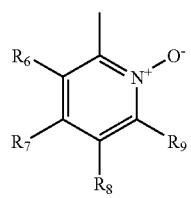
(XIa)

wherein $R_6$, $R_7$, $R_8$ and $R_9$ are as defined above for formula (X), e.g.,
wherein
a) $R_6$ is nitro, alkyl, substituted alkyl, phenyl, hydroxy, formyl, heteroalkylaryl, alkoxy, acyl or acyloxy; preferably alkyl, especially $C_{1-7}$alkyl; hydroxyl; or alkoxy, especially a $C_{1-7}$alkoxy; and
$R_7$, $R_8$ and $R_9$ are hydrogen; or
b) $R_6$, $R_8$ and $R_9$ are hydrogen; and
$R_7$ is alkyl, substituted alkyl, phenyl, halogen, alkoxy or cyano, preferably alkyl, especially $C_{1-7}$alkyl;

substituted alkyl, especially substituted $C_{1-7}$alkyl, such as —$CF_3$; or alkoxy, especially $C_{1-7}$alkoxy; or
c) $R_6$, $R_7$ and $R_9$ are hydrogen; and
$R_8$ is alkyl, substituted alkyl, halogen, nitro, cyano, thioalkoxy, acyloxy, phenyl, alkylsulfonyl or carboxyalkyl, preferably alkyl, especially $C_{1-7}$alkyl; substituted alkyl, especially —$CF_3$; halogen such as chloro, bromo or fluoro; or carboxyalkyl; or
d) $R_6$, $R_7$ and $R_8$ are hydrogen; and
$R_9$ is alkyl, halogen or hydroxy; or
e) $R_7$ and $R_9$ are hydrogen; and
each of $R_6$ and $R_8$, independently, is halogen, alkyl, substituted alkyl, phenyl or cyano; or
f) Each of $R_7$ and $R_9$ is alkyl or substituted alkyl; and $R_6$ and $R_8$ are hydrogen; or
g) $R_6$ and $R_9$ are hydrogen;
$R_7$ is alkyl or substituted alkyl; and
$R_8$ is nitro; or
h) $R_8$ and $R_9$ are hydrogen;
$R_6$ is cyano; and
$R_7$ is alkoxy; or
i) $R_7$ and $R_8$ are hydrogen; and
$R_6$ is alkyl, substituted alkyl, alkoxy or SCN; and
$R_9$ is alkyl or substituted alkyl; or
j) $R_6$ and $R_7$ are hydrogen;
$R_8$ is nitro or halogen; and
$R_9$ is alkyl or substituted alkyl; or
k) $R_6$, $R_7$, $R_8$ and $R_9$ are hydrogen; or,
l) $R_6$ and $R_7$ together with the carbon atoms to which they are attached form a phenyl group, preferably substituted with hydroxy; and
$R_8$ and $R_9$ are hydrogen; or
m) $R_6$ and $R_7$ are hydrogen; and
$R_8$ and $R_9$ together with the carbon atoms to which they are attached form a phenyl group; or
n) n is 0; or
o) n is 0;
each of $R_6$, $R_7$, $R_8$ and $R_9$, independently, is hydrogen, alkyl or halogen; and
more particularly, $R_6$, $R_7$, $R_8$ and $R_9$ are hydrogen; or
p) n is 0;
$R_6$, $R_8$ and $R_9$ are hydrogen; and
$R_7$ is alkyl; or
q) n is 0;
$R_6$, $R_7$ and $R_9$ are hydrogen; and
$R_8$ is alkyl or halogen.
In another embodiment, $R_1$ is of formula (Xb)

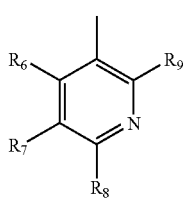

(Xb)

wherein
$R_6$, $R_7$, $R_8$ and $R_9$ are as defined above for formula (X); in particular, $R_7$ and $R_8$ together with the carbon atoms to which they are attached form a phenyl group; and $R_6$ and $R_9$ are hydrogen.

In yet another embodiment, the $R_1$ is of formula (XI)

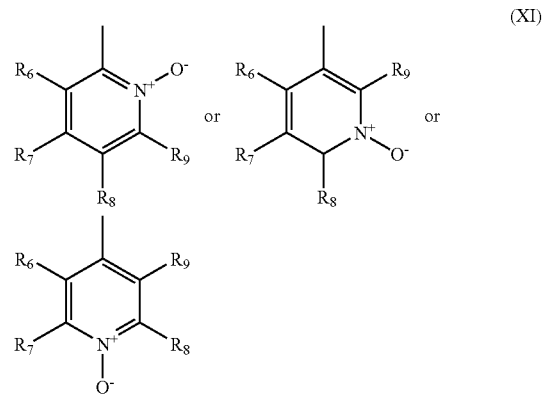

(XI)

wherein each of $R_6$, $R_7$, $R_8$ and $R_9$ independently is hydrogen, alkyl, substituted alkyl, phenyl, halogen, hydroxy or alkoxy, e.g.,
wherein
a) $R_6$ and $R_8$ are hydrogen;
$R_9$ is hydrogen or alkyl; and
$R_7$ is alkyl, substituted alkyl or phenyl; or
b) $R_6$, $R_7$ and $R_9$ are hydrogen; and
$R_8$ is halogen, alkyl or substituted alkyl; or
c) $R_7$, $R_8$ and $R_9$ are hydrogen; and
$R_6$ is hydroxy.

In a particularly useful embodiment the heteroaryl is of the formula (XIa)

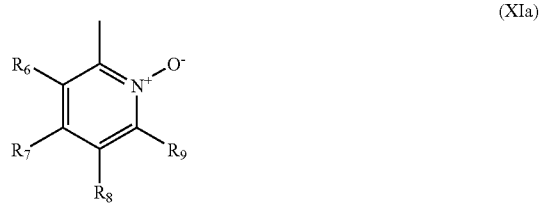

(XIa)

wherein $R_6$, $R_7$, $R_8$ and $R_9$ are as defined above for formula (XI), in particular where $R_6$, $R_7$, and $R_9$ are hydrogen and $R_8$ is fluoro.

In another embodiment, $R_1$ is an unsubstituted phenyl or the phenyl is substituted with alkoxy, e.g., methoxy; or aryloxy, e.g., phenoxy.

In another embodiment, the $R_1$ is of formula (XII)

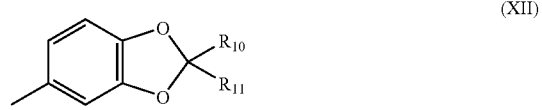

(XII)

wherein each of $R_{10}$ and $R_{11}$, independently, is hydrogen or halogen. In particular, $R_{10}$ and $R_{11}$ are both either hydrogen or both halogen.

In the compound of formula (I), M is a metal, typically a mono- or di-valent metal or an ammonium moiety. Typical metals include Mg, Ca, Na, K Li and the like. The ammonium moiety is of the formula

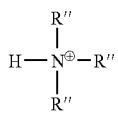

wherein R″ is hydrogen, alkyl, substituted alkyl, aryl or substituted aryl.

The ammonium moiety can be racemic or chiral. An example of an ammonium moiety is R-α-methylbenzylammonium. Examples of R″ groups include hydrogen, methyl, ethyl, propyl, butyl, phenyl, benzyl, methylbenzyl and the like.

Unless otherwise stated, the following terms as used in the specification have the following meaning.

The term "cycloalkane" or "cycloalkyl" contains from 3- to 7-ring carbon atoms, and is, e.g., cyclopropyl, cyclobutyl, cyclopentyl and cyclohexyl.

The term "azacyclo$_{4-7}$alkane" contains 1-ring heteroatom which is a nitrogen. It contains from 4-7, and especially 4- or 5-ring atoms including the heteroatom.

The term "thiazacyclo$_{4-7}$alkane" contains 2-ring heteroatoms, nitrogen and sulfur. It contains from 4-7, and especially 5-ring atoms including the heteroatoms.

The term "imidazacyclo$_{4-7}$alkane" contains 2-ring heteroatoms which are both nitrogen. It contains from 4-7, and especially 5-ring atoms including the heteroatoms.

The term "aliphatic group" refers to saturated or unsaturated aliphatic groups, such as alkyl, alkenyl or alkynyl, cycloalkyl or substituted alkyl including straight-chain, branched-chain and cyclic groups having from 1-10 carbons atoms. Preferably "alkyl" or "alk", whenever it occurs, is a saturated aliphatic group or cycloalkyl, more preferably $C_{1-7}$alkyl, particularly $C_{1-4}$alkyl. Examples of "alkyl" or "alk" include, but are not limited to, methyl, ethyl, n-propyl, isopropyl, n-butyl, isobutyl, sec-butyl, t-butyl, n-pentyl, neopentyl, n-hexyl or n-heptyl, cyclopropyl and especially n-butyl.

The term "substituted alkyl" refers to an alkyl group that is substituted with one or more substituents preferably 1-3 substituents including but not limited to, substituents, such as halogen, lower alkoxy, hydroxy, mercapto, carboxy, cycloalkyl, aryl, heteroaryl and the like. Examples of substituted alkyl groups include, but are not limited to, —CF$_3$, —CF$_2$—CF$_3$, hydroxymethyl, 1- or 2-hydroxyethyl, methoxymethyl, 1- or 2-ethoxyethyl, carboxymethyl, 1- or 2-carboxyethyl and the like.

The term "aryl" or "Ar" refers to an aromatic carbocyclic group of 6-14 carbon atoms having a single ring including, but not limited to, groups, such as phenyl; or multiple condensed rings including, but not limited to, groups, such as naphthyl or anthryl; and is especially phenyl.

The term "heteroaryl" or "HetAr" refers to a 4- to 7-membered, monocyclic aromatic heterocycle or a bicycle that is composed of a 4- to 7-membered, monocyclic aromatic heterocycle and a fused-on benzene ring. The heteroaryl has at least one hetero atom, preferably one or two heteroatoms including, but not limited to, heteroatoms, such as N, O and S, within the ring. A preferred heteroaryl group is pyridinyl, pyrimidinyl or benzdioxolanyl.

The aryl or heteroaryl may be unsubstituted or substituted by one or more substituents including, but not limited to, $C_{1-7}$alkyl, particularly $C_{1-4}$alkyl, such as methyl, hydroxy, alkoxy, acyl, acyloxy, SCN, halogen, cyano, nitro, thioalkoxy, phenyl, heteroalkylaryl, alkylsulfonyl and formyl.

The term "carbonylamine", as used herein, refers to a —NHC(O)— group wherein the amino portion of the group is linked to the aryl/heteroaryl and the carbonyl portion of the group is linked to the azacyclo$_{4-7}$alkane, thiazacyclo$_{4-7}$alkane or imidazacyclo$_{4-7}$alkane.

The term "heteroalkyl" refers to saturated or unsaturated $C_{1-10}$alkyl as defined above, and especially $C_{1-4}$heteroalkyl which contain one or more heteroatoms, as part of the main, branched or cyclic chains in the group. Heteroatoms may independently be selected from the group consisting of —NR—, where R is hydrogen or alkyl, —S—, —O— and —P—; preferably —NR—, where R is hydrogen or alkyl; and/or —O—. Heteroalkyl groups may be attached to the remainder of the molecule either at a heteroatom (if a valence is available) or at a carbon atom. Examples of heteroalkyl groups include, but are not limited to, groups, such as —O—CH$_3$, —CH$_2$—O—CH$_3$, —CH$_2$—CH$_2$—O—CH$_3$, —S—CH$_2$—CH$_2$—CH$_3$, —CH$_2$—CH(CH$_3$)—S—CH$_3$ and —CH$_2$—CH$_2$—NH—CH$_2$—CH$_2$—.

The heteroalkyl group may be unsubstituted or substituted with one or more substituents, preferably 1-3 substituents including, but not limited to, alkyl, halogen, alkoxy, hydroxyl, mercapto, carboxy and especially phenyl. The heteroatom(s) as well as the carbon atoms of the group may be substituted. The heteroatom(s) may also be in oxidized form.

The term "alkoxy", as used herein, refers to a $C_{1-10}$alkyl linked to an oxygen atom, or preferably $C_{1-7}$alkoxy, more preferably $C_{1-4}$alkoxy. Examples of alkoxy groups include, but are not limited to, groups such as methoxy, ethoxy, h-butoxy, tert-butoxy and allyloxy.

The term "acyl", as used herein, refers to the group —(O)CR, where R is alkyl, especially $C_{1-7}$alkyl, such as methyl. Examples of acyl groups include, but are not limited to, acetyl, propanoyl and butanoyl.

The term "acyloxy", as used herein, refers to the group —OC(O)R, wherein R is hydrogen, alkyl, especially $C_{1-7}$alkyl, such as methyl or ethyl, or phenyl or substituted alkyl as defined above.

The term "alkoxycarbonyl", as used herein, refers to the group —COOR, wherein R is alkyl, especially $C_{1-7}$alkyl, such as methyl or ethyl.

The term "halogen" or "halo", as used herein, refers to chlorine, bromine, fluorine, iodine and is especially fluorine.

The term "thioalkoxy", as used herein, means a group —SR, where R is an alkyl as defined above, e.g., methylthio, ethylthio, propylthio, butylthio and the like.

The term "heteroalkylaryl", as used herein, means a heteroalkyl group, e.g., —O—CH$_2$— substituted with an aryl group, especially phenyl. The phenyl group itself may also be substituted with one or more substituents, such as halogen, especially fluoro and chloro; and alkoxy such as methoxy.

The term "alkylsulfony", as used herein, means a group —SO$_2$R, wherein R is alkyl especially $C_{1-7}$alkyl, such as methyl sulfonyl.

"Protecting group" refers to a chemical group that exhibits the following characteristics: 1) reacts selectively with the desired functionality in good yield to give a protected substrate that is stable to the projected reactions for which protection is desired, 2) is selectively removable from the protected substrate to yield the desired functionality; and 3) is removable in good yield by reagents compatible with the other functional group(s) present or generated in such projected reactions. Examples of suitable protecting groups may be found in Greene et al., "Protective Groups in Organic Synthesis", 3$^{rd}$ Ed., John Wiley & Sons Inc., NY (1999). Preferred hydroxy protecting groups include benzyl, Fmoc, TBDMS, photolabile protecting groups, such as Nvom, Mom and Mem. Other preferred protecting groups include NPEOC and NPEOM.

It will be appreciated that the compounds disclosed herein may exist in the form of optical isomers, racemates or diastereoisomers. In particular, in the compounds disclosed herein where $R_4$ and $R_5$ are different, the carbon atom to which the $R_4$ and $R_5$ groups are bonded is a chiral center and such compounds can exist in the R, S or racemic forms. It is preferred that the process of the invention prepares the R optically pure form. By "optically pure" is meant that the enantiomeric purity is greater than 50%, preferably greater than 80%, more preferably greater than 90%, and most preferably greater than 95%. The optically pure R isomer of compound (I) can be used, in which case all subsequent compounds in the synthesis will remain in the R optically pure form, with respect to the same chiral carbon atom. If an optically pure compound is used as the starting material, purification from the undesired diastereomer can be avoided at later steps. Such R form of compound (I) is represented below:

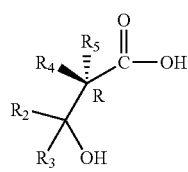

(I)

wherein $R_2$, $R_3$, $R_4$ and $R_5$ are as defined above. The optically pure form of compound (I) is novel provided that when either $R_4$ or $R_5$ is hydrogen, the other substituent, i.e., $R_4$ or $R_5$ is not hydrogen or methyl. In a particular embodiment of the novel compound of formula (I), $R_5$ is hydrogen and $R_4$ is $C_{2-10}$alkyl, in a more particular embodiment $C_{2-7}$alkyl, and in a even more particular embodiment $C_4$alkyl.

In a further embodiment an optically pure compound of formula (I) t $R_2$, $R_3$, and $R_5$ are hydrogen and $R_4$ is alkyl; such a compound has the structure (Ia):

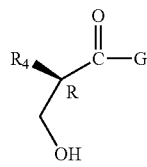

(Ia)

Another embodiment in compound (I) is where $R_4$ is n-butyl, where such compound has the structure (Ib)

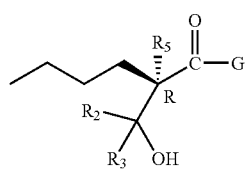

(Ib)

Another embodiment is where $R_2$, $R_3$ and $R_5$ are hydrogen and $R_4$ is n-butyl; such compound has the structure (Ic):

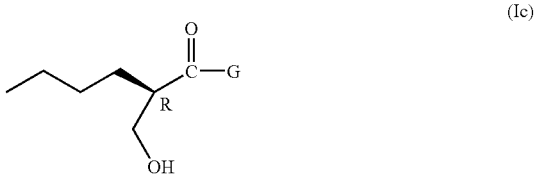

(Ic)

More particular examples of the optically pure compound of formula (I) are as follows:

(Id)

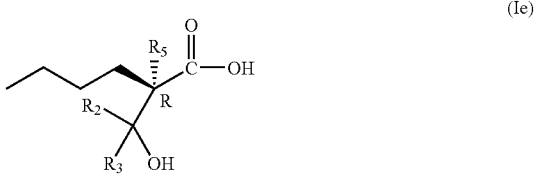

(Ie)

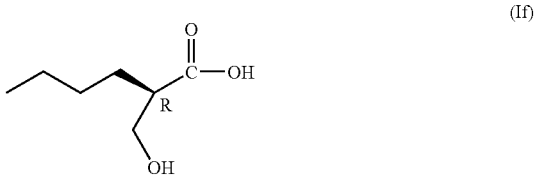

(If)

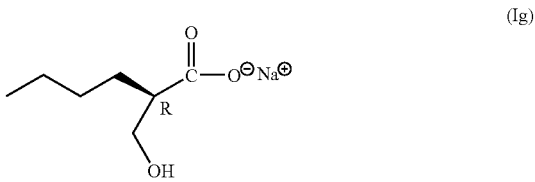

(Ig)

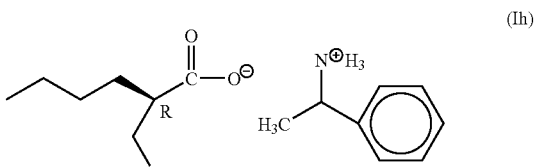

(Ih)

Alternatively, the racemate form of compound (I) can be used and then the R form can be resolved at a later step and the R form used for subsequent steps. For example, the compound formed after opening the β-lactam ring, i.e., compound (VII), the product of Step D, can be resolved into its RS and SS diastereomers and only the RS diastereomer used for subsequent steps. The RS diastereomer of compound (VII) is depicted below:

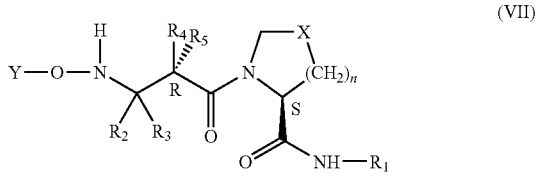

(VII)

wherein $R_2$, $R_3$, $R_4$ $R_5$ Y, X, $R_1$ and n are as defined above, provided that $R_4$ and $R_5$ are different.

The diastereoisomers are resolved using standard techniques known in the art, for example, using silica gel column chromatography and an ethyl acetate/hexane solvent system (see, e.g., the methods taught in Chapter 4 of "Advanced Organic Chemistry", $5^{th}$ edition, J. March, John Wiley and Sons, NY (2001)).

In the compounds disclosed herein, the following significances are specific embodiments individually or in any subcombination:

1. $R_1$ is a heteroaryl of formula (IIa), wherein $R_6$, $R_7$ and $R_9$ are hydrogen and $R_8$ is methyl or trifluoromethyl; or $R_6$, $R_7$ and $R_8$ are hydrogen and $R_9$ is fluoro; or $R_6$, $R_8$ and $R_9$ are hydrogen and $R_7$ is ethyl or methoxy; or $R_7$, $R_8$ and $R_9$ are hydrogen and $R_6$ is hydroxy; or $R_7$ and $R_8$ are hydrogen, $R_6$ is methoxy and $R_9$ is methyl; or $R_1$ is a heteroaryl of formula (IIIa), wherein $R_6$, $R_7$ and $R_9$ are hydrogen and $R_8$ is fluoro or trifluoromethyl; or $R_6$, $R_8$ and $R_9$ are hydrogen and $R_7$ is ethyl; preferably $R_1$ is a heteroaryl of formula (IIa), wherein $R_6$, $R_8$ and $R_9$ are hydrogen and $R_7$ is ethyl or a heteroaryl of formula (IIIa), wherein $R_6$, $R_7$ and $R_9$ are hydrogen and $R_8$ is fluoro.
2. X is —$CH_2$—, —CH(OH)—, —CH(OR)—, —$CF_2$— or —CH(F)—, preferably X is —$CH_2$—;
3. $R_4$ is alkyl, preferably $C_{1-7}$alkyl, such as n-butyl;
4. n is 1.

Temperature and pressure are not known to be critical for carrying out any of the steps of the invention, i.e., Steps A through E. Generally, for any of the steps, a temperature of about −10° C. to about 150° C., preferably about 0° C. to about 80° C., is typically employed. Typically about atmospheric pressure is used for convenience; however, variations to atmospheric pressure are not known to be detrimental. Oxygen is not known to be detrimental to the process, therefore for convenience the various steps can be performed under ambient air, although an inert atmosphere, such as nitrogen or argon, can be used if desired. For convenience equimolar amounts of reactants are typically used; however molar ratios can vary from about 1 to 2 equivalents, relative to the other reactant. The pH for the various steps is typically about 2 to about 12. The solvent used for the various steps are typically organic solvents, although in some situations aqueous/organic solvents can be used. Examples of suitable solvents include dioxane; mtehylene chloride; dichloromethane; toluene, acetone; methyl ethyl ketone; THF; isopropyl acetate; DMF; alcohols, especially higher branched alcohols, such as t-butanol; and the like.

For Step A, a typical temperature is about 0° C. to about 50° C., preferably about 5° C. to about 35° C.; and a typical reaction time is about 1 hour to about 10 hours, preferably about 2 hours to about 5 hours. A pH of about 2 to about 7, preferably about 3 to about 5, more preferably about 4, is typically employed. The carboxy-activating agent can be for example, DCC, CDMT, EDCl and the like. The amount of carboxy-activating agent employed is typically about 0.5 to about 2 molar equivalents relative to compound (I). The solvent is water or a mixture of water and one or more organic solvents, such as THF, dioxane, alcohols, such as methanol, ethanol and the like. Specific examples of solvents include THF/water and water. In the event that an ammonium salt of compound (I) is used in the process, the salt will be dissolved in water containing at least a molar equivalent amount of base, such as alkaline metal hydroxide, such as NaOH and KOH; the base is added to liberate the free amine which is extracted into the organic phase, the aqueous phase is used for the coupling reaction.

For Step B, a typical temperature is about −20° C. to about 25° C., more typically about −5° C. to about 5° C.; and a typical reaction time is about 1 hour to about 2 hours, more typically about 2 hours to about 5 hours. For Step B, an alcoholic solvent should not be used. For reactant (XIII), X' is preferably chloro and R' is preferably lower alkyl or phenyl, with $CH_3SO_2Cl$ and tosyl chloride being most typical. The pH for Step B is basic and is typically about 9 to about 10. The base used for Step B can be any conventional base known in the art that will activate the hydroxy group of compound (III), and such base will be used in a hydroxyl-activating amount which is at least about 1 molar equivalent relative to compound (III). The base can also act as solvent in which case it will be present in a solvating amount which is in excess of the above amount. Examples of bases that can be employed include pyridine; DMAP; a trialkylamine, e.g., trimethylamine; resin-bound bases; Hunig bases; and the like. A particular solvent is pyridine, THF or EtOAc.

For cyclization Step C, a typical temperature is about 20° C. to about 150° C., more typically about 40° C. to about 80° C.; and a typical reaction time is about 1 hour to about 20 hours, more typically about 2 hours to about 4 hours. The pH for Step C is basic, typically, about 8 to about 12. The base used in Step C can be any base known in the art that is capable of de-protonating the amide group of compound (IV). Examples of suitable bases include inorganic or organic bases, such as potassium carbonate; lithium carbonate; sodium carbonate; lithium bicarbonate; sodium bicarbonate; alkyl lithium, e.g., butyl lithium; and the like. The amount of base employed is a de-protonating amount which is typically in molar excess to the amount of compound (IV), e.g., about 1-5 equivalents relative to compound (IV). For certain solvents, such as THF, dioxane, dimethoxyethane and the like, it may be necessary to use a catalytic amount of a phase transfer catalyst, such as trialkylarylammonium salt or a tetraalkylammonium salt, e.g., tetrabutylammonium chloride or tetrabutylammonium bromide. The examples of solvents are ketones, such as acetone or methylethylketone.

For Step D, a typical temperature is about 30° C. to about 150° C., more typically about 60° C. to about 80° C.; and a typical reaction time is about 3 hours to about 20 hours, more typically about 5 hours to about 10 hours. The pH for Step D is typically about 5 to about 11. The activator for Step D is a compound which protonates the β-lactam keto oxygen; such activators include, e.g., mild (weak) organic acids, such as branched or unbranched carboxylic acids, e.g., 2-ethylhexanoic acid, acetic acid, isobutryic acid and the like. If an aqueous alcoholic solvent is used an activator is not needed; examples ofd aqueous alcoholic solvents include $MeOH.H_2O$, $EtOH.H_2O$ and the like. If an activator is used a typical solvent is THF, dioxane or dimethoxyethane. If an activator is used it is used in an protonating amount which is typically about 0.1 molar equivalents to about 2 molar equivalents relative to compound (V).

For Step E, a typical temperature is about −30° C. to about 50° C., more typically about 0° C. to about 25° C.; and a typical reaction time is about 10 minutes to about 5 hours, more typically about 20 minutes to about 1 hour. The pH for Step E is not critical and can vary considerably. For Step E the solvent should not be an alcoholic solvent. The formylating agent can be, for example, $HCO_2H/Ac_2O$, trifluoroethylformate, and the like, and is present in a formylating amount which is typically about 1 molar equivalent to about 2 molar equivalents relative to compound (VII). A typical solvent is EtOAc, isopropylacetate, t-butylacetate or THF.

For Step F, a typical temperature is about 10° C. to about 35° C., more typically about 20° C. to about 22° C.; and a typical reaction time is about 60 minutes to about 18 hours, more typically about 4 hours to about 8 hours. The pH for Step F is typically about 4 to about 8. The solvent for Step F is typically an organic solvent, i.e., ethyl acetate, iso-propyl acetate, methylene chloride, and the like. The oxidizing agent can be a conventional agent known in the art, e.g., as disclosed in March, "Advanced Organic Chemistry", Chapter 19, 5$^{th}$ edition, Wiley Interscience, NY, incorporated herein by reference. Typical oxidizing agents include urea/hydrogen peroxide with phthalic anhydride; magnesium monoperoxyphthalate (MMPP); MCPBA, Oxone (available from Aldrich), and the like.

Insofar as the production of starting materials is not particularly described, the compounds are known or may be prepared analogously to methods known in the art or as disclosed in the examples hereinafter.

The following abbreviations are used:
Ac=acetyl
CDMT=chlorodimethoxy triazine
DIEA=diisopropylethylamine
DCC=dicyclohexylcarbodiimide
DMAP=dimethylaminopyridine
DMF=dimethylformamide
EDCl=1-(3-dimethylaminopropyl)-3-ethylcarbodiimide hydrochloride
2-EHA=2-ethylhexanoic acid
EtOAc=ethyl acetate
EtOH=ethanol
Fmoc=9-fluorenylmethyl-oxycarbonyl
HPLC=high performance liquid chromatography
MeOH=methanol
Mom=methoxy methyl ether
Mem=methoxy ethoxy methyl ether
NPEOC=4-nitrophenethyloxycarbonyl
NPEOM=4-nitrophenethyloxy-methyloxycarbonyl
Nvom=nitroveratryl oxymethyl ether
TBDMS=t-butyidimethylsilyl,
TMSCI=trimethylsilyl chloride
RT=room temperature
THF=tetrahydrofuran The following examples illustrate the process of the invention but should not be interpreted as a limitation thereon:

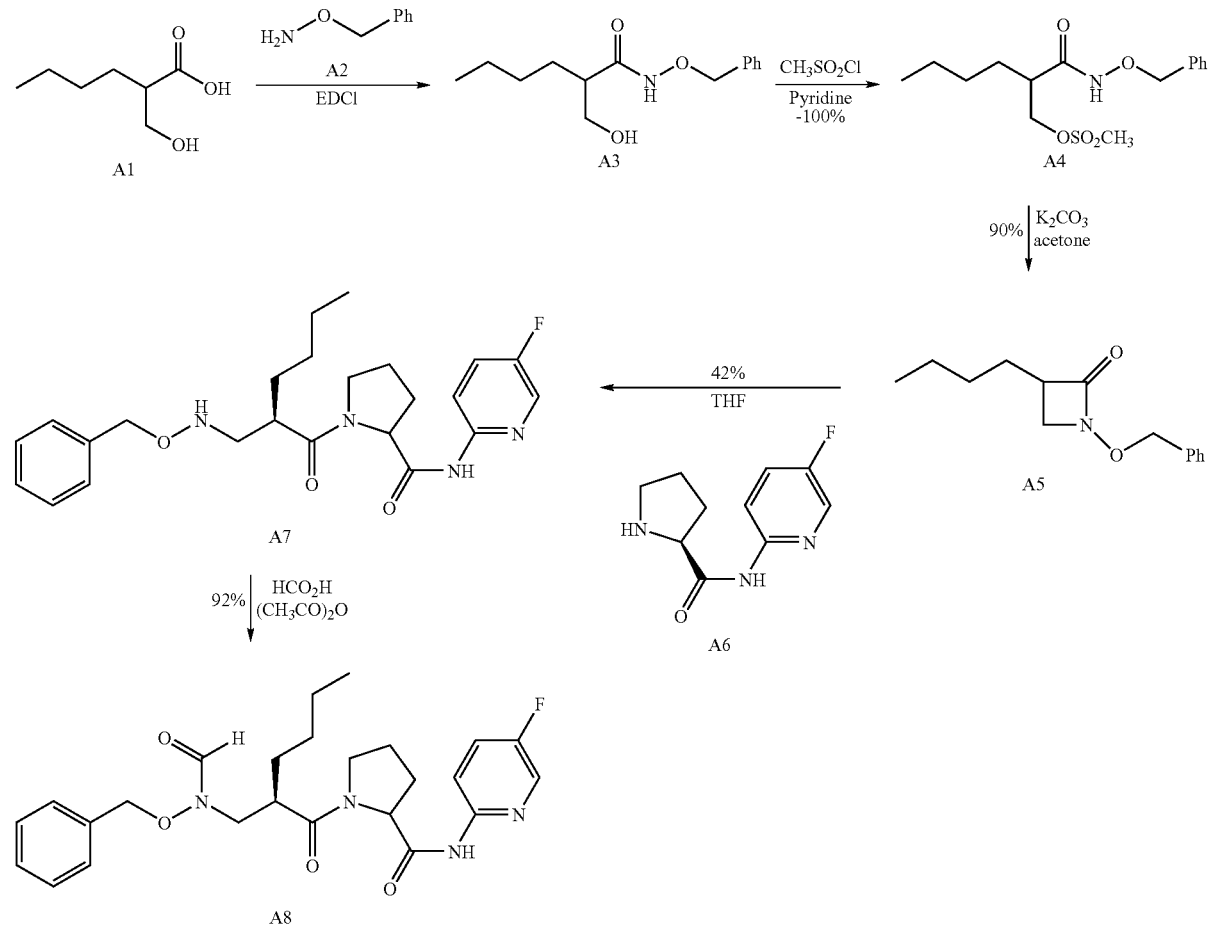

Reaction Scheme I

Product numbers in the following examples refer to reaction scheme I depicted immediately above.

Product A3

A flask was charged with 2.80 g (19.2 mmol) of A1, 80 mL of THF, 20 mL of water, and 4.73 g (38.4 mmol) of A2. The resulting solution was stirred at RT and the pH of the solution was adjusted to 4.2-4.5 with 2N HCl acid solution.

5.52 g (28.8 mmol) of EDCl was added in three portions (2.12 g, 2.26 g, 1.14 g) within 15 minutes. The resulting solution was stirred at RT for 2 hours, and the pH of the solution was adjusted to 4.2-4.5 during the reaction. The progress of the reaction was monitored by HPLC. After the reaction was completed, THF was evaporated under reduced pressure, and the residue was extracted with 3×70 mL of ethyl acetate and the combined organic phase was washed sequentially with 2×50 mL of 10% citric acid solution, 50 mL of water, 2×50 mL of 5% sodium bicarbonate solution and 50 mL brine dried over MgSO$_4$. The evaporation of organic solvent afforded 2.4 g of A3 (94% yield).

Product A4

A flask was charged with 7.53 g (30 mmol) of A3 and 30 mL of pyridine. The resulting solution was cooled to 0±2° C. with ice-salt bath. Then, 2.78 mL (36 mmol) of methanesulfonyl chloride was slowly added and maintained the temperature at 0±2° C. for 1.5 hours. After the reaction monitored by HPLC was completed, the mixture was poured into cold 120 mL of 1N HCl acid, and extracted with 2×100 mL of ethyl acetate. The organic phase was washed sequentially with 2×70 mL of 1N HCl acid until the aqueous solution was acidic, 100 mL of saturated sodium bicarbonate solution, 100 mL of brine and dried over MgSO$_4$. The evaporation of organic solvent gave 9.87 g of A4 (~100% yield).

Product A5

A flask was charged with 16.07 g (116 mmol) of potassium carbonate (powdered), 631 mL of acetone. The suspension was heated to reflux. Then, 12.49 g (38 mmol) of A4 in 91 mL of acetone was slowly added (30 minutes). The resulting mixture was stirred at reflux for 1 hour. After the reaction monitored by HPLC was completed, the suspension was filtered through celite, and washed with 200 mL of ethyl acetate. The organic solvent was concentrated and diluted with 400 mL of ethyl acetate and washed with 100 mL of 1N HCl acid, 100 mL of saturated sodium bicarbonate solution, 100 mL of brine and dried over MgSO$_4$. The concentration of organic solvent under reduced pressure afforded 7.96 g of A5 (liquid, 90% yield).

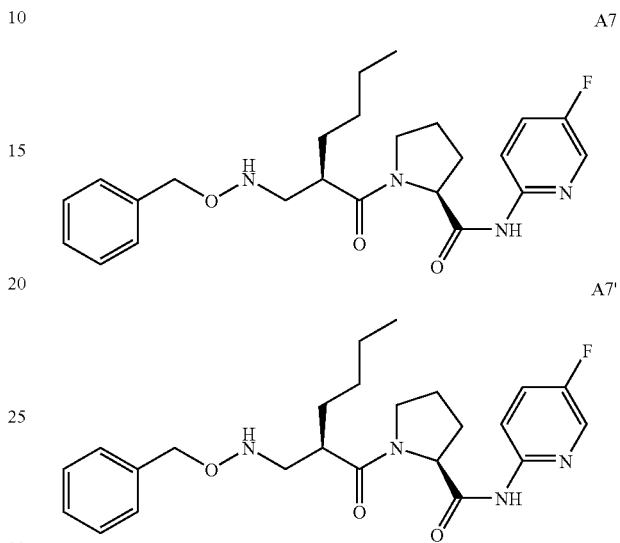

When the A5 is racemic, attacking with chiral A6 results in two diastereomers A7 and A7' They can be separated by silica gel column using EtOAc and hexanes (1:1) as eluent system. A7 was the second fraction from column and it was identified by comparing with the authentic sample from the other approach.

There are several methods to open the β-lactam ring in A5. The results for opening the lactam ring are summarized in Table 1.

TABLE 1

Reaction Conditions and Results for Coupling A5 and A6

| A5 | A6 | Solventy | Additives | Temp. (° C.) | Time (h) | Remarks |
|---|---|---|---|---|---|---|
| 5 mmol | 6 mmol | MeOH (25 ml) | | 22 | 1 | None |
| | | | | 65 | 1 | None |
| | | | 0.1 mL - 2 EHA | 66 | 1 | Non |
| | | | 1 mL - H2O | 22 | 15 | None |
| | | | 1 mL - H2O | 70 | 2 | None |
| | | MeOH (5 mL) | 2 mL - H2O | 82 | 17 | 100% conversion |
| 5 mmol | 7.5 mmol | Toluene | | 115 | 3 | None |
| | | | 0.5 mL - TMSCI | 116 | 4 | 3% conversion |
| | | | 1 mL - 2EHA | 115 | 3 | 100% conversion one bypd. |
| 5 mmol | 6 mmol | THF | 0.2 mL - 2EHA | 70 | 7 | 98% conversion |

Product A7 and A7'

A flask was charged with 1.165 g (5 mmol) of A5, 10 mL of THF, 1.24 g (6 mmol) of A6 and 0.2 mL (1.25 mmol) of 2-ethyl hexanoic acid. The resulting solution was heated to reflux (70° C.) for 7 hours, and the reaction was monitored by HPLC. THF was evaporated and the residue was dissolved in 100 mL of ethyl acetate. The organic layer was washed sequentially with 25 mL of water, 25 mL of saturated sodium bicarbonate, 25 mL of brine and dried over $MgSO_4$. The concentration of organic solvent gave oil which was further purified by column separation on silica gel to give 0.95 g of A7 and 0.85 g of A7' (84% total yield).

Product A8

A small flask was charged with 0.35 g (3.43 mmol) of acetic anhydride, and cooled to <10° C. Then, 0.50 g (10.8 mmol) of formic acid (96%) was slowly added to the it (25 minutes). After the addition, the solution was warmed to RT and stirred at this temperature for 30 minutes.

A flask was charged with 0.62 g (1.40 mmol) of A7 and 5 mL of ethyl acetate. The solution was cooled to −3 to 0° C. with ice-salt bath. Then, the solution prepared from above procedure was slowly added (30 minutes). After addition, the reaction was completed (monitored by HPLC). The solution was diluted with 100 mL of ethyl acetate, and washed sequentially with 25 mL of water, 2×25 mL of saturated sodium bicarbonate, 25 mL of brine and dried over $MgSO_4$. The organic solvent was evaporated to give 0.61 g of A8.

The lactam ring can also be opened by a base, such as lithium hydroxide. As depicted below, the opening ring product was obtained in 91.5% yield with high purity after work-up.

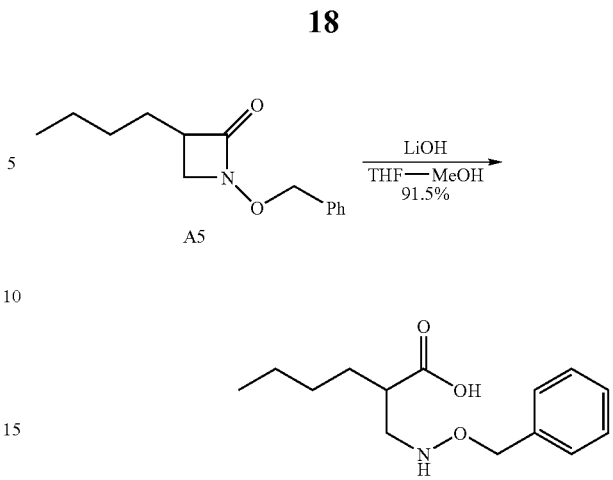

A flask was charged with 1.165 g (5 mmol) of A5, 15 mL of THF, 5 mL of methanol. The resulting solution was cooled to 0° C. Then, 0.25 g of lithium hydroxide monohydrate in 5 mL of water was added. The solution was stirred and allowed to warm to 22° C. for 18 hours. After the reaction monitored by HPLC was completed, the pH of the mixture was adjusted to 2 with 2N HCl acid. The organic solvents were removed, and the residue was extracted with 2×50 mL of ethyl acetate, and washed with 2×30 mL of brine and dried over $MgSO_4$. The evaporation the organic solvent gave 1.15 g of desired product in 91.5% yield with high purity.

Reaction Scheme II

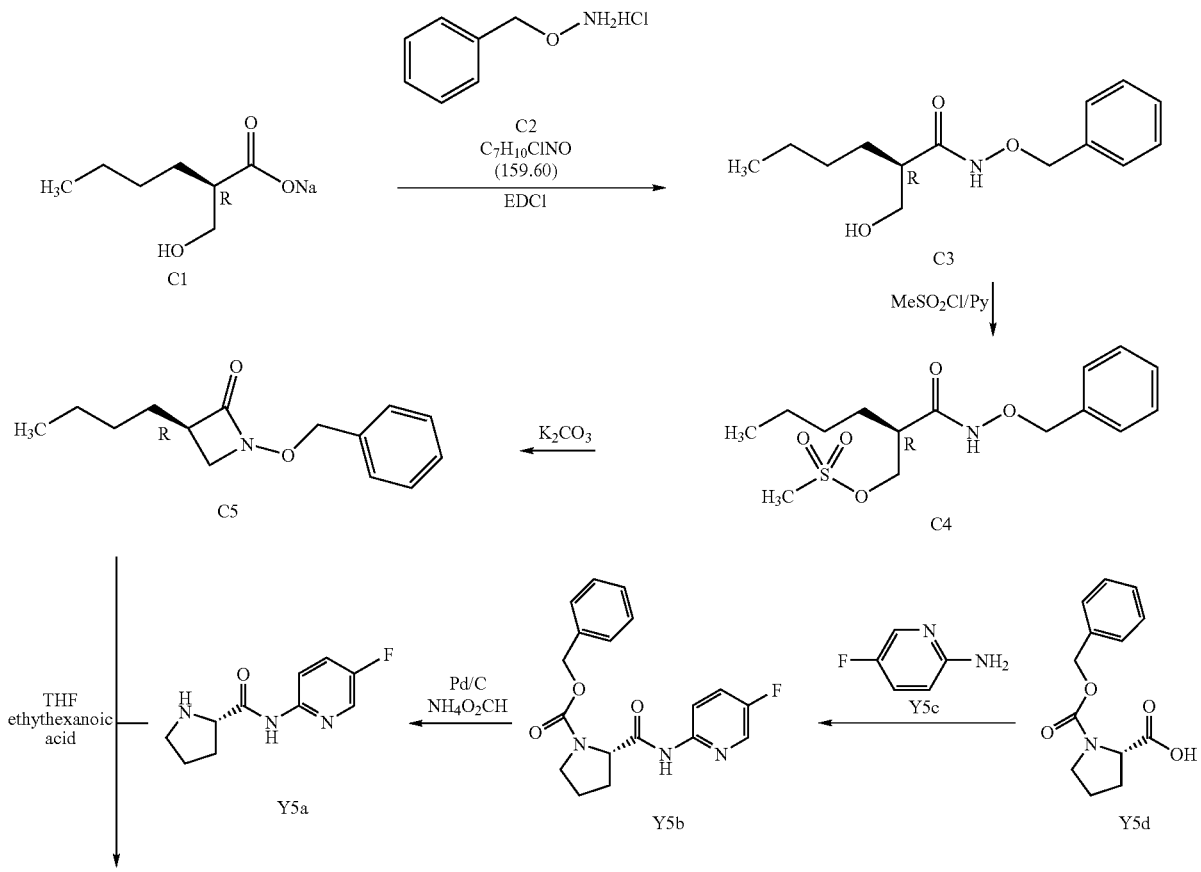

-continued

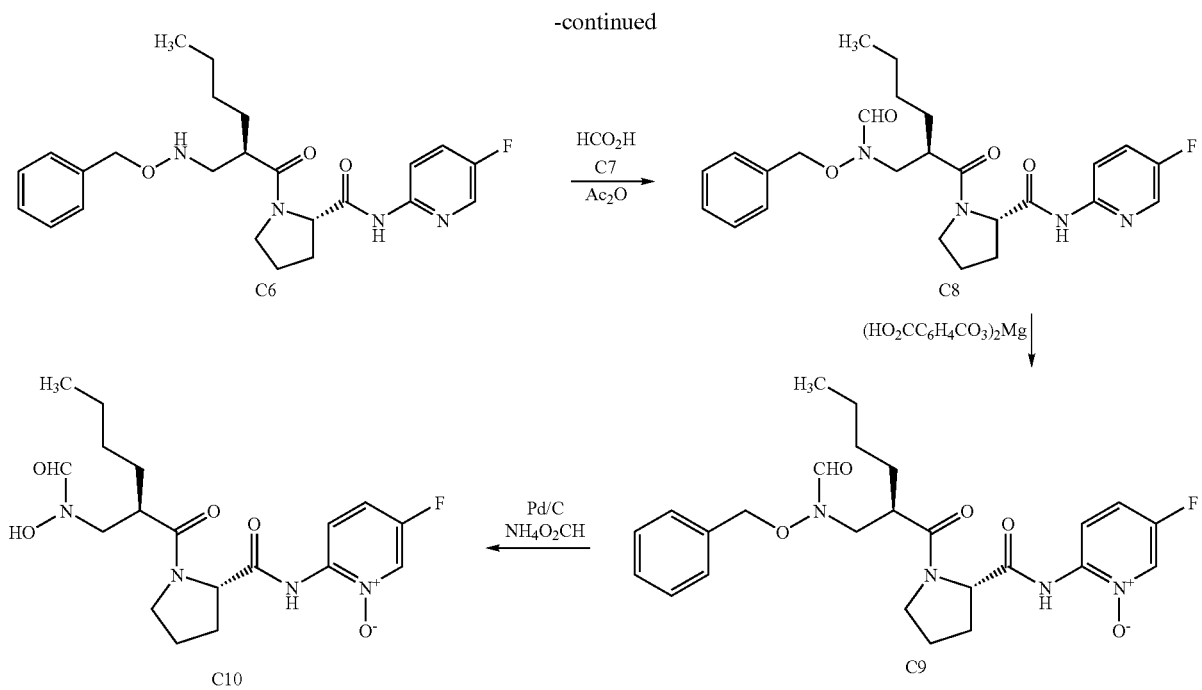

The product numbers in the following examples refer to Reaction Scheme II depicted immediately above.

Compound C3

From (2R)-2-(hydroxymethyl)hexanoic acid:

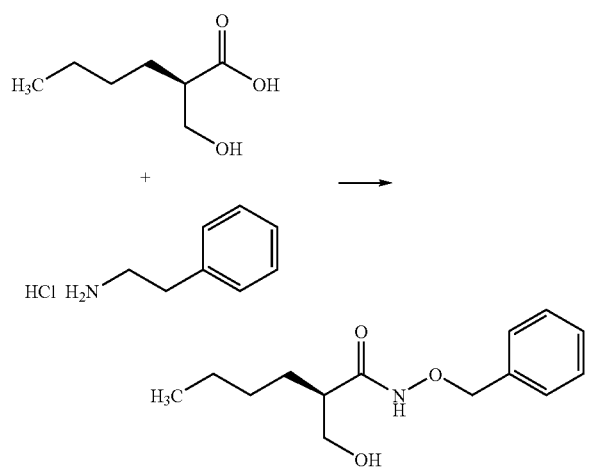

A 5 L, 4-necked, round-bottomed flask, equipped with a mechanical stirrer, digital thermometer and nitrogen inlet-outlet, is charged with 102.39 g of (2R)-2-(hydroxymethyl)hexanoic acid, 123.0 g of O-benzylhydroxylamine hydrochloride and 2.25 L of water. Adjust the pH by adding one equivalent of NaOH to a pH of 4-5. Stir the reaction mixture at 18° C.±3° C. (external temperature: 15-18° C.) for 30 minutes to give a cloudy solution. Add 161.3 g of 1-[3-(dimethylamino)propyl]-3-ethylcarbodiimide hydrochloride (EDCl) over a period of 60 minutes in 6 portions, while maintaining the internal temperature at 18° C.±3° C. (external temperature: 10° C.±3° C.). Wash the funnel once with 50 mL of water. Stir the thick suspension at 20° C.±3° C. for 2 hours. Filter the solids through a polypropylene filter cloth and a Büchner funnel then wash the flask and filter cake once with 0.5 L of water. Air-dry the cake at 20° C.±3° C. (house vacuum) for 2 hours, then dry the wet cake (~265 g weight) at 65° C.±3° C. (15 mbar) for 24 hours to give 162 g of (2R)-2-(hydroxymethyl)-N-(phenylmethoxy)hexanamide (C3) as a white solid in 95% yield. m.p. 100-102° C.; $[\alpha]_D^{25}$=+0.556 (c, 1.0, MeOH).

From Sodium Salt:

A 5 L, 4-necked, round-bottomed flask, equipped with a mechanical stirrer, digital thermometer and nitrogen inlet-outlet, is charged with 117.8 g of (2R)-2-(hydroxymethyl)hexanoic acid sodium salt, 123.0 g of O-benzylhydroxylamine hydrochloride, and 2.25 L of water.

Stir the reaction mixture at 18° C.±3° C. (external temperature: 15-18° C.) for 30 minutes to give a cloudy solution. Add 161.3 g of 1-[3-(dimethylamino)propyl]-3-EDCl over a period of 60 minutes in 6 portions, while maintaining the internal temperature at 18° C.±3° C. (external temperature: 10° C.±3° C.). Wash the funnel once with 50 mL of water. Stir the thick suspension at 20° C.±3° C. for 2 hours. Filter the solids through a polypropylene filter cloth and a Büchner funnel then wash the flask and filter cake once with 0.5 L of water. Air-dry the cake at 20° C.±3° C. (house vacuum) for 2 hours, then dry the wet cake (~265 g weight) at 65° C.±3° C. (15 mbar) for 24 hours to give 162 g of (2R)-2-(hydroxymethyl)-N-(phenylmethoxy)hexanamide (C3) as a white solid in 95% yield. m.p. 100-102° C.; $[\alpha]_D^{25}$=+0.556 (c, 1.0, MeOH).

From R-α-methylbenzylammonium Salt:

A 12 L, 4-necked, round-bottomed flask, equipped with a mechanical stirrer, digital thermometer and nitrogen inlet-outlet, is charged with 300 g of (2R)-2-(hydroxymethyl)hexanoic acid R-α-methylbenzylammonium salt and 1.12 L of water and 2.2 L of tert-butyl methyl ether. Cool the suspension to an internal temperature at 18-22° C. over a period of 20 minutes and add a solution of 94.24 g aqueous NaOH (50% w/w). Stir the solution for 30 minutes and separate layers. Wash the aqueous layer with 2.2 L of tert-butyl Methyl ether. Separate layers and save the aqueous layer containing the (2R)-2-(hydroxymethyl)hexanoic acid sodium salt and proceed as mentioned in Example 1 to get compound 3 in 91% yield; m.p. 100-102° C.; $[\alpha]_D^{25}$=+0.556 (c, 1.0, MeOH).

Alternatively the corresponding potassium, lithium or calcium salts of (2R)-2-(hydroxymethyl)hexanoic acid were also used in this step as described in Example 2.

In addition, any other ammonium salts of (2R)-2-(hydroxymethyl)hexanoic acid can be used after removing the amine component as described in Example 3.

Compounds C3→C4

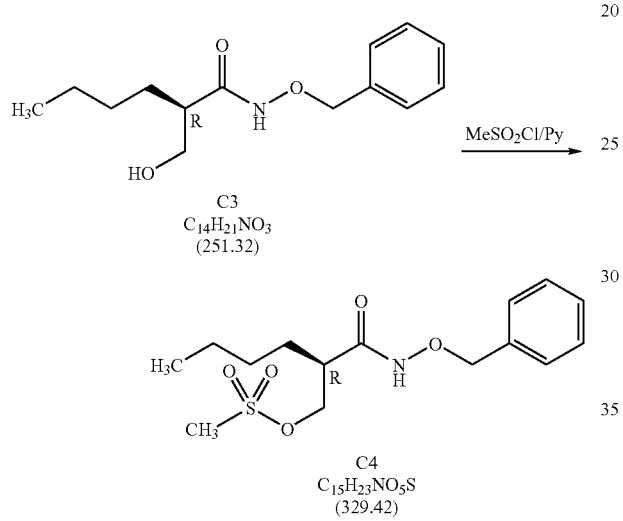

A flask was charged with 7.53 g (30 mmol) of C3, and 15 mL of pyridine. The resulting solution was cooled to 0±4° C. with ice-salt bath. Then, 2.78 mL (42 mmol) of methanesulfonyl chloride was slowly added and maintained temperature at 0±4° C. for 2 hours. After the reaction monitored by HPLC was completed, the mixture was quenched by slow addition of 95 mL of 2N HCl at −5±5° C., then warmed to RT and stirred at this temperature for 2 hours. The solids were filtered and washed with water (30 mL), dried in an oven at 50° C. for 14 hours to give 9.86 g of C4 (~100% yield); $[\alpha]_D^{25}$=+5.901 (c, 1.0, MeOH).

Compound C5

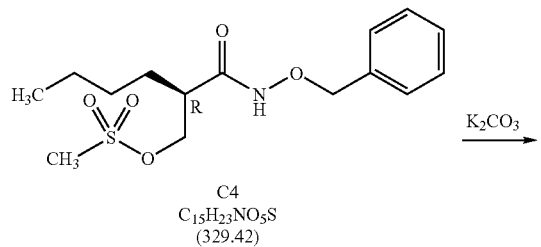

-continued

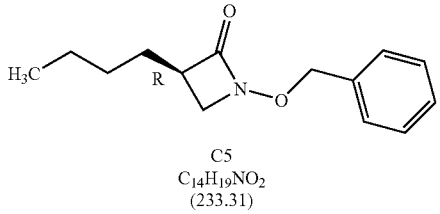

C5
C14H19NO2
(233.31)

A flask was charged with 3.86 (27.8 mmol) of potassium carbonate, 50 mL of THF and 0.3 g of tetrabutylammonium bromide. The suspension was heated to 40° C. and stirred at this temperature for 30 minutes. Then, 3.0 g (9.1 mmol) of C4 was added in one portion. The mixture was heated to 60° C. and stirred at this temperature for 1 hour. After the reaction, is completed as monitored by HPLC, the solid was filtered and washed with 20 mL of THF. The organic solvent was concentrated to 8.58 mL/g (THF/C5) for the following step without further purification. The pure C5: $[\alpha]_D^{25}$=+24.63 (c, 1.0, MeOH).

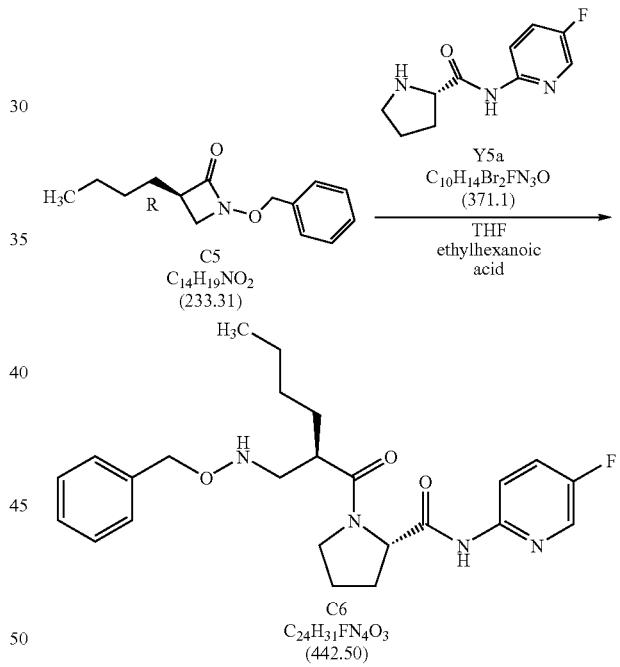

Compound C6

A flask was charged with 2.12 g (9.1 mmol) of C5 from previous experiment in 20 mL of THF, 2.26 g (10.9 mmol) of Y5a and 0.8 mL of 2-ethyl hexanoic acid. The resulting solution was heated to reflux (70° C.) for 8 hours, and the reaction was monitored by HPLC. THF was evaporated and the residue was dissolved in 50 mL of ethyl acetate.

The organic layer was washed sequentially with 20 mL of water 2×20 mL of 1 N HCl solution, 20 mL of saturated sodium bicarbonate and 20 mL of brine. The concentration of organic solvent gave 3.78 g of C6 (94% yield) in 21 mL of ethyl acetate which was used for the following step. The pure C6: $[\alpha]_D^{25}$=−74.43 (c, 1.0, MeOH).

Step C6+C7→C8

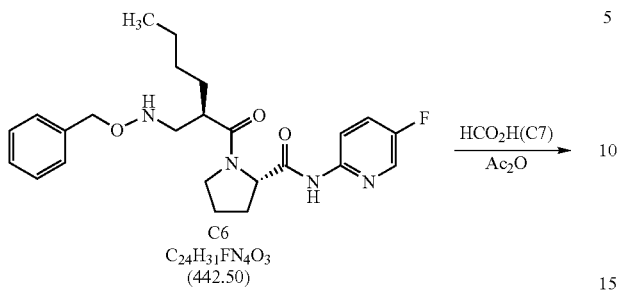

C6
C$_{24}$H$_{31}$FN$_4$O$_3$
(442.50)

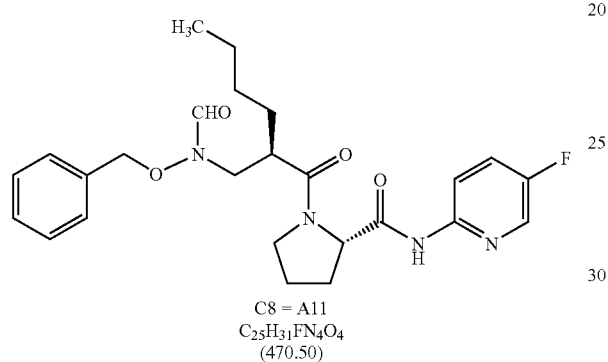

C8 = A11
C$_{25}$H$_{31}$FN$_4$O$_4$
(470.50)

A flask was charged with 22.6 g (0.22 mole) of acetic anhydride, and cooled to <10° C. Then, 32.3 g (0.674 mole) of formic acid (96%) was slowly added to the flask (25 minutes), and maintained the temperature between 5-10° C. After addition, the solution was warmed to RT and stirred at this temperature for 30 minutes.

A flask was charged with 36 g (81.4 mmol) of C6 and 200 mL of ethyl acetate. The solution was cooled to −5° C. to −10° C. with methanol-ice bath. Then, the solution prepared from above procedure was slowly added (30 minutes). After the reaction was completed (monitored by HPLC). The solution was diluted with 100 mL of water and warmed to 10° C., and stirred for 20 minutes. The organic layer was washed sequentially with 3×100 mL of saturated sodium bicarbonate, 100 mL of brine. Added 374 mL of ethyl acetate, and distilled ethyl acetate under vacuum in house vacuum until the residue volume about 274 mL. Heated the solution >50° C., and added 822 mL of heptane while maintaining the temperature <50° C. Cooled the solution to 10° C., and seeded with Plant A11. Maintained the temperature of the suspension at 0-5° C. for 4 hours, then warmed to RT (24° C.) for 14 hours, cooled to −5° C. to −10° C. for 3 hours. The solid was filtered and washed with 100 mL of cold heptane/ethyl acetate (4/1 by volume) and dried to give 24.0 g of C8 in 63% yield. The pure C8: $[\alpha]_D^{25}$=−97.02 (c, 1.0, MeOH).

What is claimed is:

1. A process for preparing a compound of the formula (VIII)

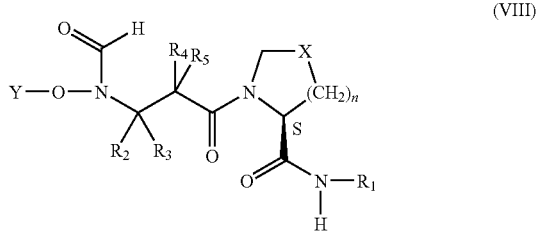

(VIII)

comprising step A:
   contacting a compound of the formula (I)

(I)

with a compound of the formula (II)

Y—O—NH$_2$    (II)

in the presence of a carboxy activating agent, in a suitable solvent under conditions suitable to form a compound of the formula (III)

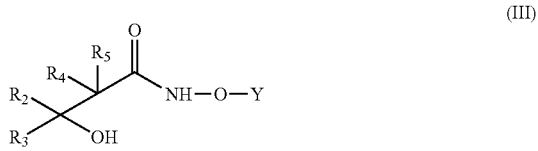

(III)

followed by step B:
   contacting compound (III) with a compound of the formula (XIII)

R'—SO$_2$—X'    (XIII)

in the presence of a base in a suitable solvent, under conditions suitable to form a compound of the formula (IV)

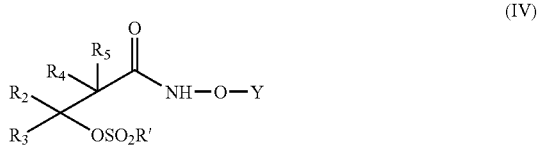

(IV)

followed by Step C:
   contacting compound (IV) with a base in a suitable solvent under conditions suitable to form a compound of the formula (V)

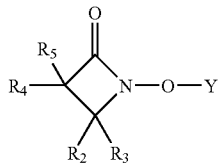

followed by Step D:
contacting compound (V) with a compound of the formula (VI)

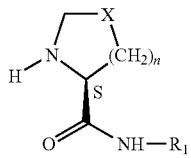

in a suitable solvent optionally in the presence of an activator under conditions suitable to form a compound of the formula (VII)

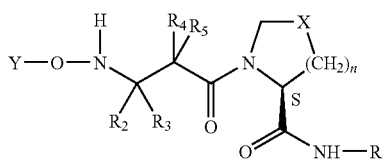

followed by Step E:
contacting compound (VII) with a formylating agent in a suitable solvent under conditions suitable to form compound (VIII);
wherein
Y is a hydroxy protecting group;
Each of $R_2$, $R_3$, $R_4$ and $R_5$, independently, is hydrogen or an aliphatic group;
X is —$CH_2$;
G is —OH or —$O^{\ominus}M^{\oplus}$, wherein M is a metal or an ammonium moiety;
$R_1$ is aryl or heteroaryl;
X' is halo;
R' is alkyl or aryl; and
n is 1.

2. The process of claim 1, followed by additional Step F which comprises contacting the compound of formula (VIII), wherein $R_1$ is heteroaryl having an N heteroatom, with an oxidizing agent to form the corresponding N-oxide derivative.

3. The process of claim 1, followed by the additional step of removing the hydroxyl-protecting group by contacting compound (VIII) with a palladium catalyst to form the compound of formula (IX)

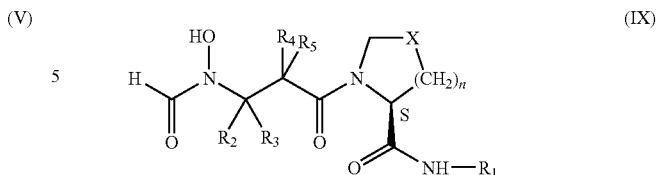

wherein $R_1$, $R_2$, $R_3$, $R_4$, $R_5$, X and n are as defined above.

4. The process of claim 1, wherein each of $R_2$, $R_3$ and $R_5$ is hydrogen; $R_4$ is butyl; X is —$CH_2$—; n is 1; Y is benzyl or t-butyldimethylsilyl; and $R_1$ is of the formula

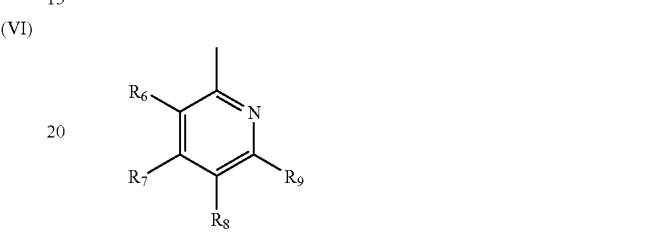

wherein
$R_6$ and $R_9$ are hydrogen;
$R_7$ is hydrogen or $C_{1-7}$alkyl; and
$R_8$ is hydrogen, halogen or $C_{1-7}$alkyl.

5. The process of claim 4, wherein $R_7$ is hydrogen; and $R_8$ is fluoro.

6. The process of claim 4, wherein $R_7$ is $C_{1-7}$ alkyl; and $R_8$ is hydrogen.

7. The process of claim 1, wherein $R_1$ is of the formula (XIa)

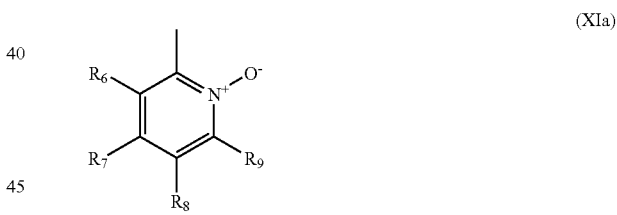

wherein
$R_6$, $R_7$ and $R_9$ are hydrogen; and
$R_8$ is halogen or $C_{1-7}$alkyl.

8. The process of claim 7, wherein $R_8$ is fluoro.

9. The process of claim 1, carried out at a temperature of about 0° C. to about 80° C., a pH of about 2 to about 12, and in one or more solvents selected from the group consisting of dioxane, methylene chloride, dichloromethane, toluene, acetone, methyl ethyl ketone, THF, isopropyl acetate, DMF and an alcohol.

* * * * *

UNITED STATES PATENT AND TRADEMARK OFFICE
CERTIFICATE OF CORRECTION

| | | |
|---|---|---|
| PATENT NO. | : 7,589,216 B2 | Page 1 of 1 |
| APPLICATION NO. | : 10/527628 | |
| DATED | : September 15, 2009 | |
| INVENTOR(S) | : Kapa et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1148 days.

Signed and Sealed this

Twenty-eighth Day of September, 2010

David J. Kappos
*Director of the United States Patent and Trademark Office*